(12) United States Patent
Tudela

(10) Patent No.: US 11,419,280 B2
(45) Date of Patent: Aug. 23, 2022

(54) METHODS OF CROSSBREEDING FUNGI ORGANISMS

(71) Applicant: Jerred Tudela, Lebanon, OR (US)

(72) Inventor: Jerred Tudela, Lebanon, OR (US)

( * ) Notice: Subject to any disclaimer, the term of this patent is extended or adjusted under 35 U.S.C. 154(b) by 0 days.

(21) Appl. No.: 17/383,921

(22) Filed: Jul. 23, 2021

(65) Prior Publication Data

US 2022/0007604 A1    Jan. 13, 2022

(51) Int. Cl.
  *A01H 1/02*    (2006.01)
  *A01H 15/00*   (2006.01)
(52) U.S. Cl.
  CPC .............. *A01H 1/022* (2021.01); *A01H 1/021* (2021.01); *A01H 15/00* (2013.01)
(58) Field of Classification Search
  CPC ................................ A01H 1/021; A01H 1/022
  See application file for complete search history.

(56) References Cited

PUBLICATIONS

Boekhout et al Mycological Research vol. 106, No. 11, pp. 1251-1261 (Year: 2002).*
J.B. Routien Mycologia vol. 32, pp. 97-104 (Year: 1940).*

* cited by examiner

*Primary Examiner* — David H Kruse
(74) *Attorney, Agent, or Firm* — Mohr Intellectual Property Law Solutions, PC

(57) ABSTRACT

Methods of crossbreeding fungi organisms. The methods include placing a first fungus organism on a first growth medium. The first fungus organism is selected from the genus *Psilocybe* or *Panaeolus*. The methods further include placing a second fungus organism on the first growth medium adjacent to the first fungus organism. The second fungus organism is selected from the genus *Psilocybe* or *Panaeolus* and is different than the first fungus organism. The methods include allowing the first fungus organism to replicate to form a first colony and allowing the second fungus organism to replicate to form a second colony. The methods further include allowing the first colony and the second colony to expand until they intersect along a clamp line where the first colony and the second colony exchange genetic material between them to yield a crossbred fungus organism.

20 Claims, 25 Drawing Sheets

METHODS OF CROSSBREEDING FUNGI ORGANISMS

BACKGROUND

The present disclosure relates generally to methods of crossbreeding fungi organisms. In particular, methods of crossbreeding different fungi organisms from the genera *Psilocybe* and *Panaeolus* are described.

Fungi from the genera *Psilocybe* and *Panaeolus* can be found growing naturally all over the world. Most, or nearly all, the species of *Psilocybe* contain the psychoactive compounds psilocybin, psilocin, and baeocystin. Some *Panaeolus* species, such as *Panaeolus cyanescens*, produce high concentrations of those compounds as well. The concentration of the psychoactive compounds varies across all the different species and sub-variants of species, with certain species and sub-variants consistently producing higher concentrations than the other species or sub-variants.

*Psilocybe* and *Panaeolus* fungi have a long history of use among native peoples of Mesoamerica for divination, religious communion, and healing. As of 2021, research is being conducted on the use of psilocybin, psilocin, and baeocystin in therapeutic contexts.

Traditionally *Psilocybe cubensis* and *Panaeolus cyanescens* are the two most cultivated species of *Psilocybe* and *Panaeolus* genus fungi. *Psilocybe cubensis* and *Panaeolus cyanescens* are the most cultivated because they prefer tropical and subtropical climates and naturally distribute on dung, mulch, and other rich soils, which makes it possible to easily cultivate them indoors.

Advanced *Psilocybe* and *Panaeolus* cultivators have been successful in crossbreeding two different sub-variants of the species *Psilocybe cubensis* by using a less than ideal technique. Conventional techniques to crossbreed two different *Psilocybe cubensis* species sub-variants involve using a microscope to isolate single spores from the two different sub-variants, via serial spore dilution, and germinating the two single spores together. When the spores germinate, they form what is called homokaryotic mycelium. This homokaryotic mycelium consists of *Monokaryon* or uninucleate cells.

When two monokaryons come in contact with each other, the hyphal cell walls break open in a process called hyphal anastomosis fusion. Hyphal anastomosis fusion allows for the nuclei of two vegetatively compatible hyphal cells to move into the mycelia of the other *Monokaryon*. The distinct nuclei moving into the myceia of the other *Monokaryon* results in the formation of binucleate cells in what would now be dikaryotic mycelium. This combination of cells from both parental spores creates a new sub-variant that carries genetic information from both those spores. When this dikaryotic mycelium is spawned to a nutrient rich substrate and provided with the necessary conditions to induce fruiting, hybrid fruit bodies of the same species (*Psilocybe cubensis*) will form.

The existing method of crossbreeding two different *Psilocybe cubensis* species sub-variants just described does not always work due to multiple known complications. One known complication is that the chances of germination are greatly reduced when spores are diluted to single spores. Another known complication is that the two monokaryotic hyphal mycelium from each spore must be vegetatively compatible.

Another limitation of this conventional crossbreeding method is that it works only with spore producing *Psilocybe* fungi belonging to the same species, i.e., *Psilocybe cubensis*. No method for crossbreeding sporeless mushrooms, abnormal mutations of mushrooms, sclerotia or truffles, or any combination of these fungi currently exists.

There is a wide range of potential benefits to breeding and introducing a greater diversity of species and strains or sub-variants of *Psilocybe* and *Panaeolus* fungi. Novel strains or species may exhibit novel characteristics. For example, novel strains or species may exhibit higher concentration of psychoactive compounds, faster growth, an improved ability to be cultivated indoors, and/or unique color of spores. A wide variety of other unique phenotypes may be exhibited. The unique phenotypes may be desirable to cultivate for therapeutic use or for aesthetic purposes. For example, albino, leucistic, or mutation type fruit bodies may have unique aesthetic appeal.

Thus, there exists a need for methods of crossbreeding fungi organisms that improve upon and advance the design of known fungi crossbreeding methods. Examples of new and useful fungi crossbreeding methods relevant to the needs existing in the field are discussed below. Examples of existing references relevant to methods of crossbreeding fungi organisms include U.S. patent references U.S. Pat. No. 5,563,317A, US20040144020A1, U.S. Pat. No. 6,521,817B2, and US20120167256A1. The complete disclosures of the above patents and patent applications are herein incorporated by reference for all purposes.

SUMMARY

The present disclosure is directed to methods of crossbreeding fungi organisms. The methods include placing a first fungus organism on a first growth medium. The first fungus organism is selected from the genus *Psilocybe* or *Panaeolus*. The methods further include placing a second fungus organism on the first growth medium adjacent to the first fungus organism. The second fungus organism is selected from the genus *Psilocybe* or *Panaeolus* and is different than the first fungus organism. The methods include allowing the first fungus organism to replicate to form a first colony and allowing the second fungus organism to replicate to form a second colony. The methods further include allowing the first colony and the second colony to expand until they intersect along a clamp line where the first colony and the second colony exchange genetic material between them to yield a crossbred fungus organism.

DETAILED DESCRIPTION

Figure 1:
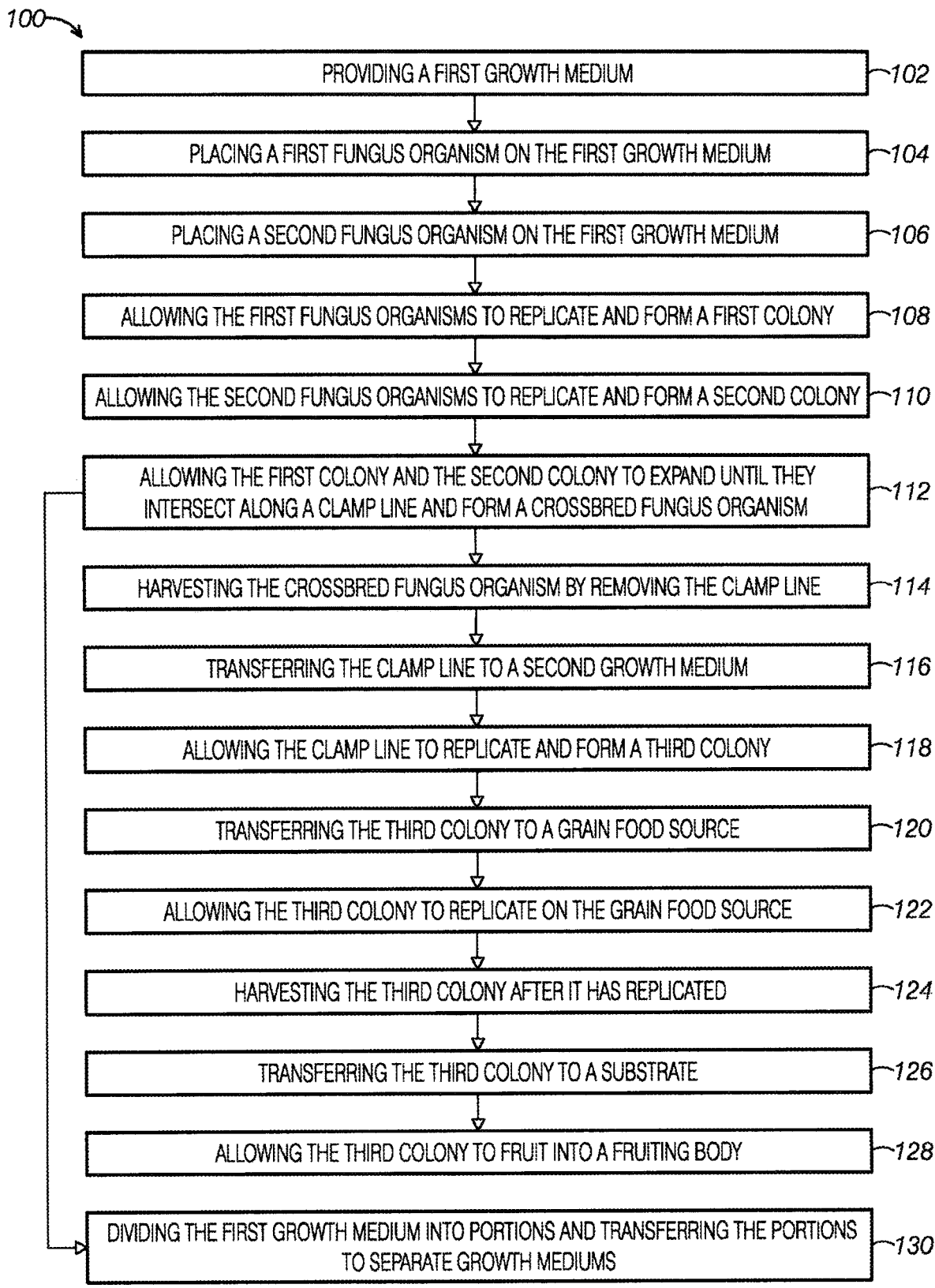
FIG. 1 is a flow diagram of a method of crossbreeding fungi organisms.
Figure 2:
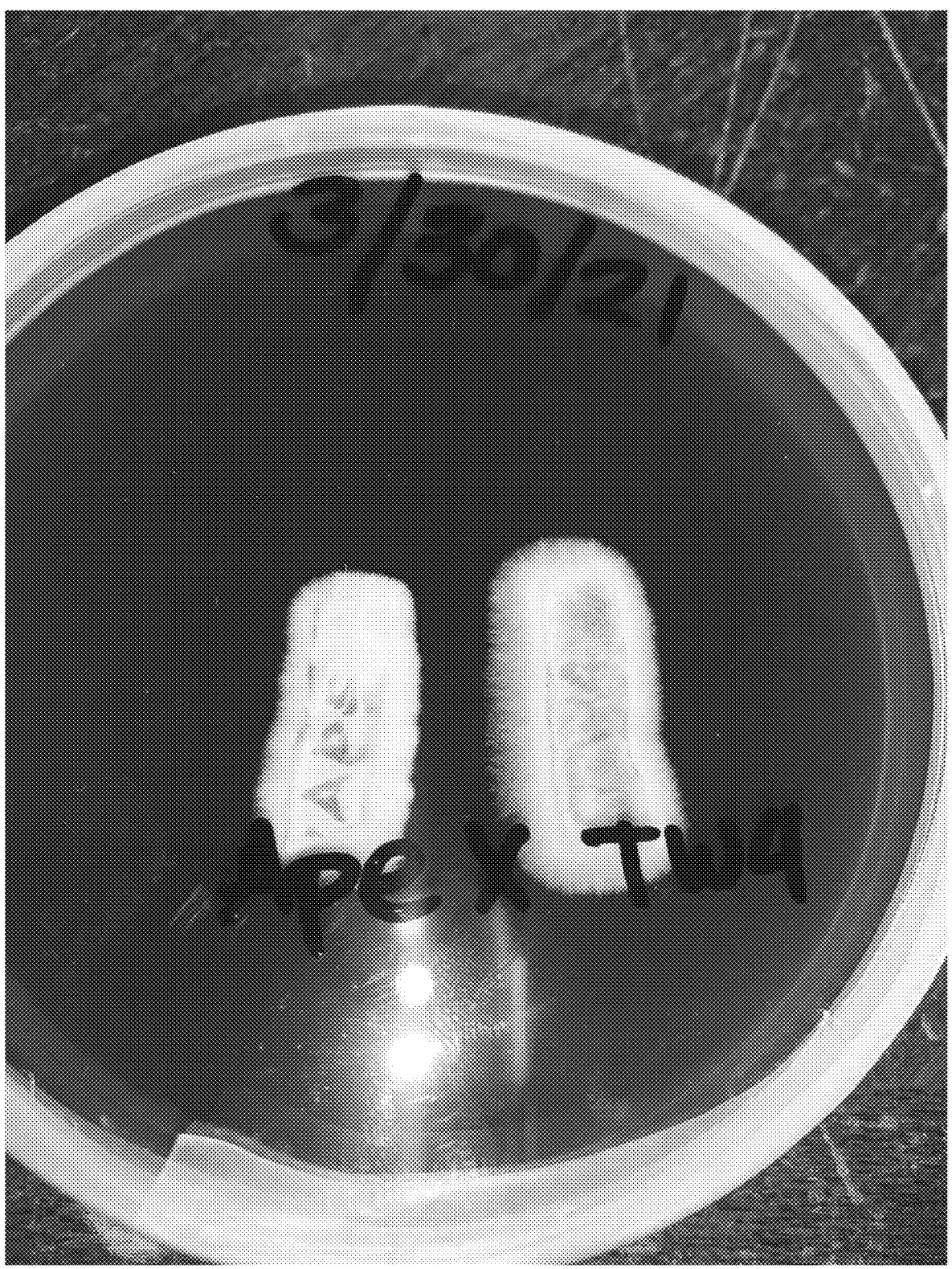
FIG. 2 is a photograph of agar wedges of dikaryotic mycelium, Ape and Tidal Wave 4, placed together on a nutrient rich agar medium.
Figure 3:
FIG. 3 is a photograph of the dikaryotic mycelium shown in FIG. 2 growing towards each other.
Figure 4:
FIG. 4 is a photograph of the dikaryotic mycelium shown in FIG. 3 intersecting and forming a clamp line.
Figure 5:
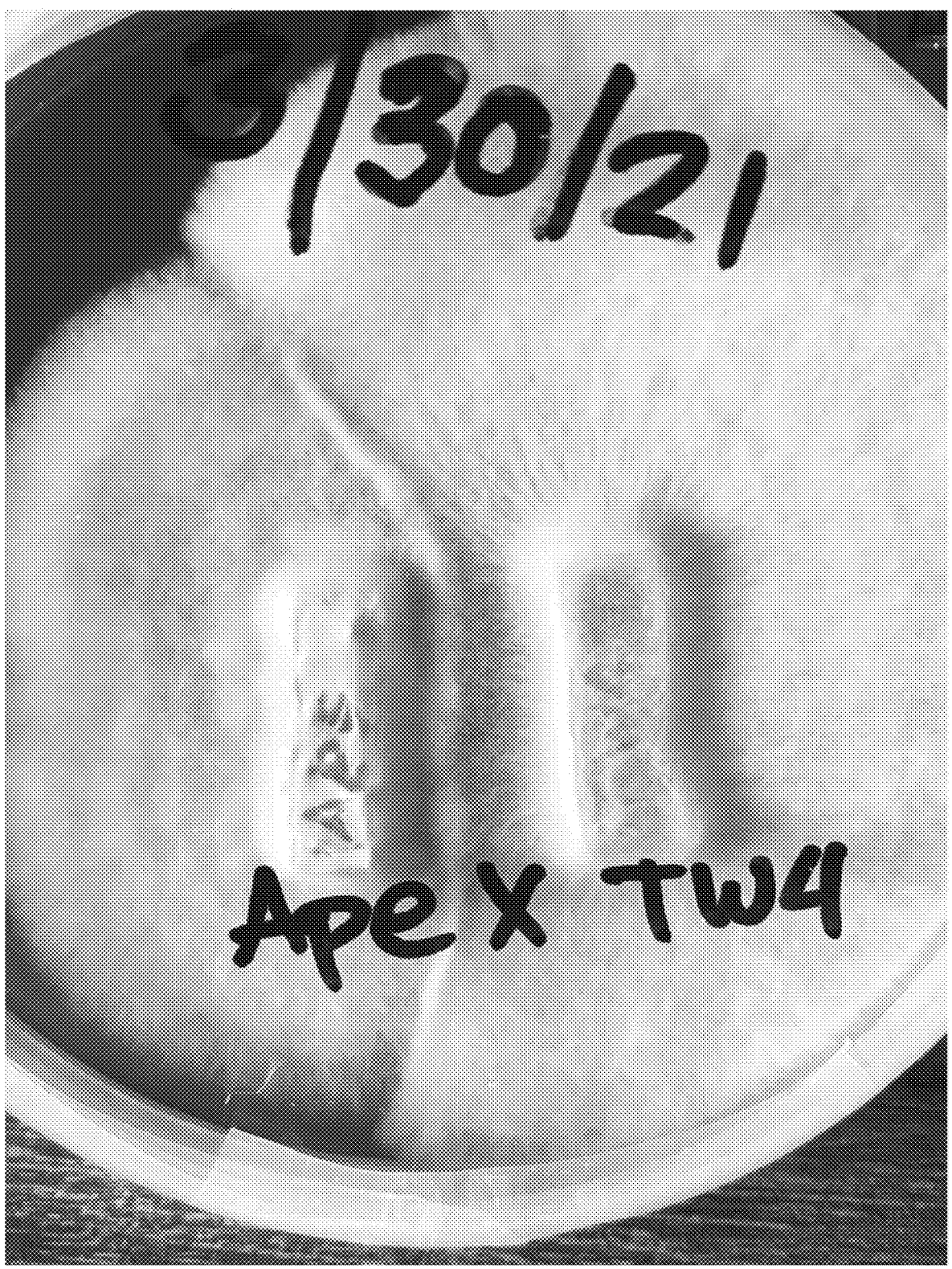
FIG. 5 is a photograph of the dikaryotic mycelium shown in FIG. 2 forming a crossbred fungus organism within the clamp line.
Figure 6:
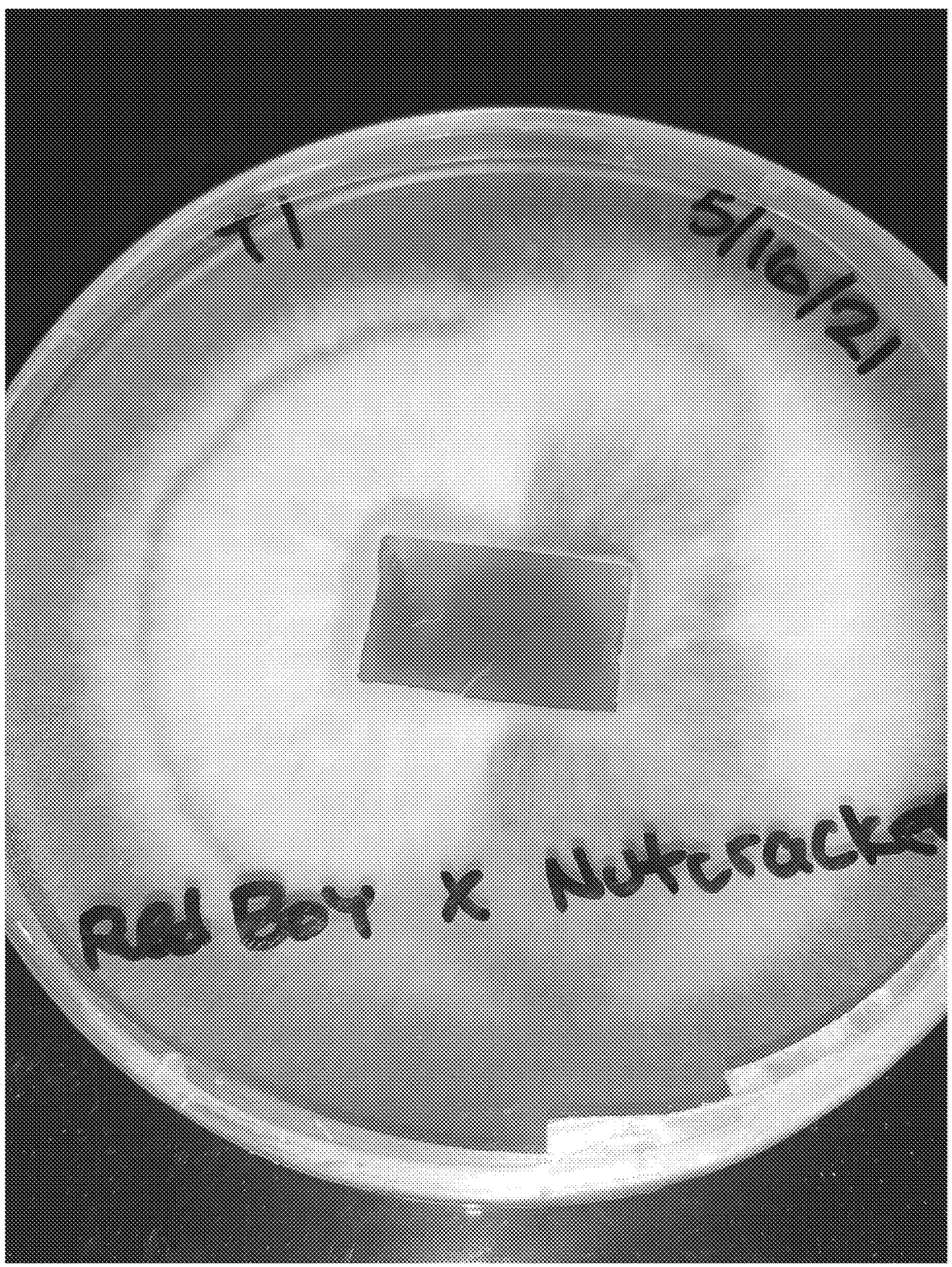
FIG. 6 is a photograph of a crossbred fungus organism harvested from a clamp line between Red Boy and Nutcracker fungi organisms replicating on a second growth medium.
Figure 7:
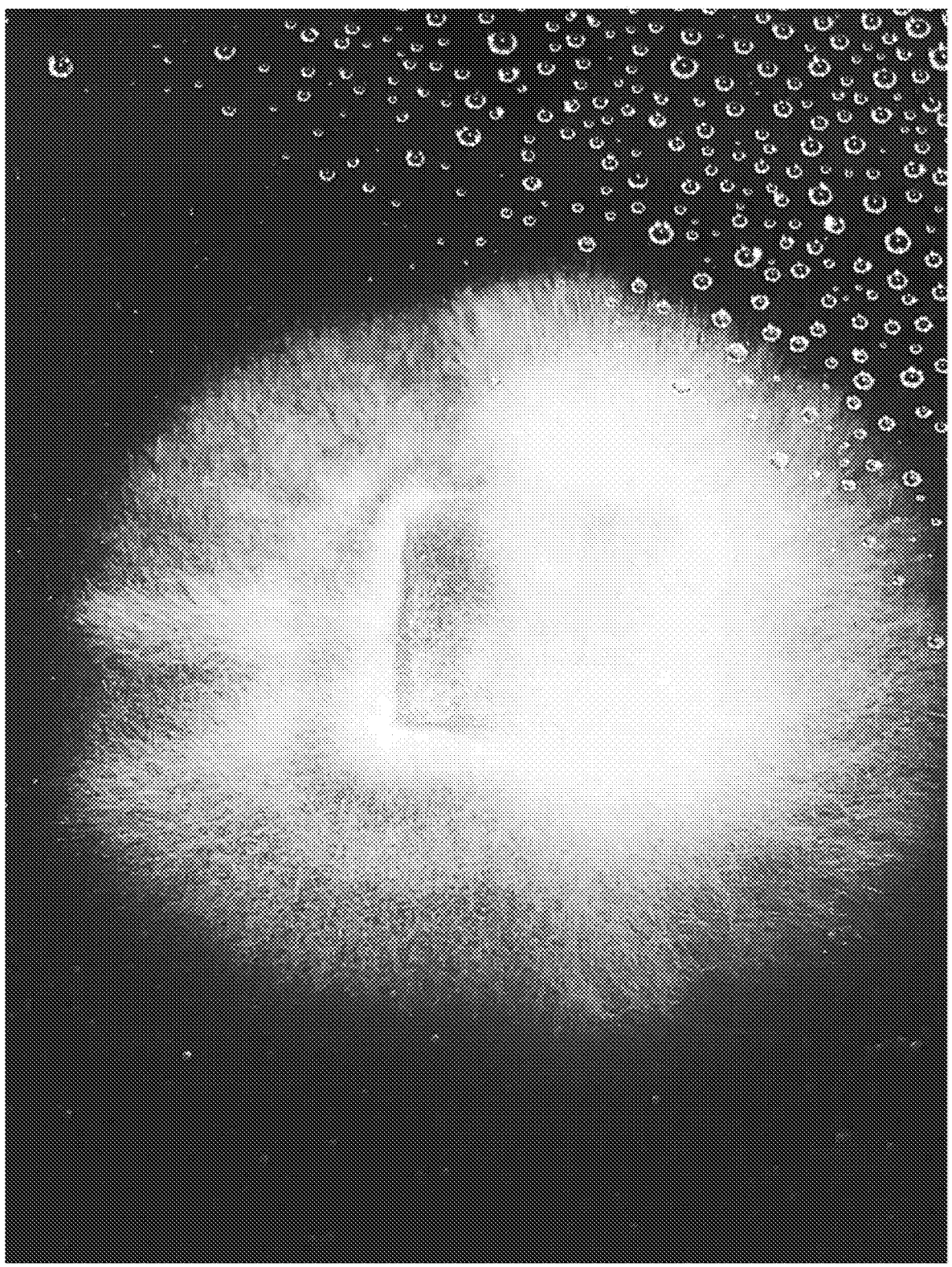
FIG. 7 is a photograph of the crossbred fungus organism shown in FIG. 6 after replicating for approximately six hours depicting noticeable growth pattern changes, such as increased vigor and aggressiveness.
Figure 8:
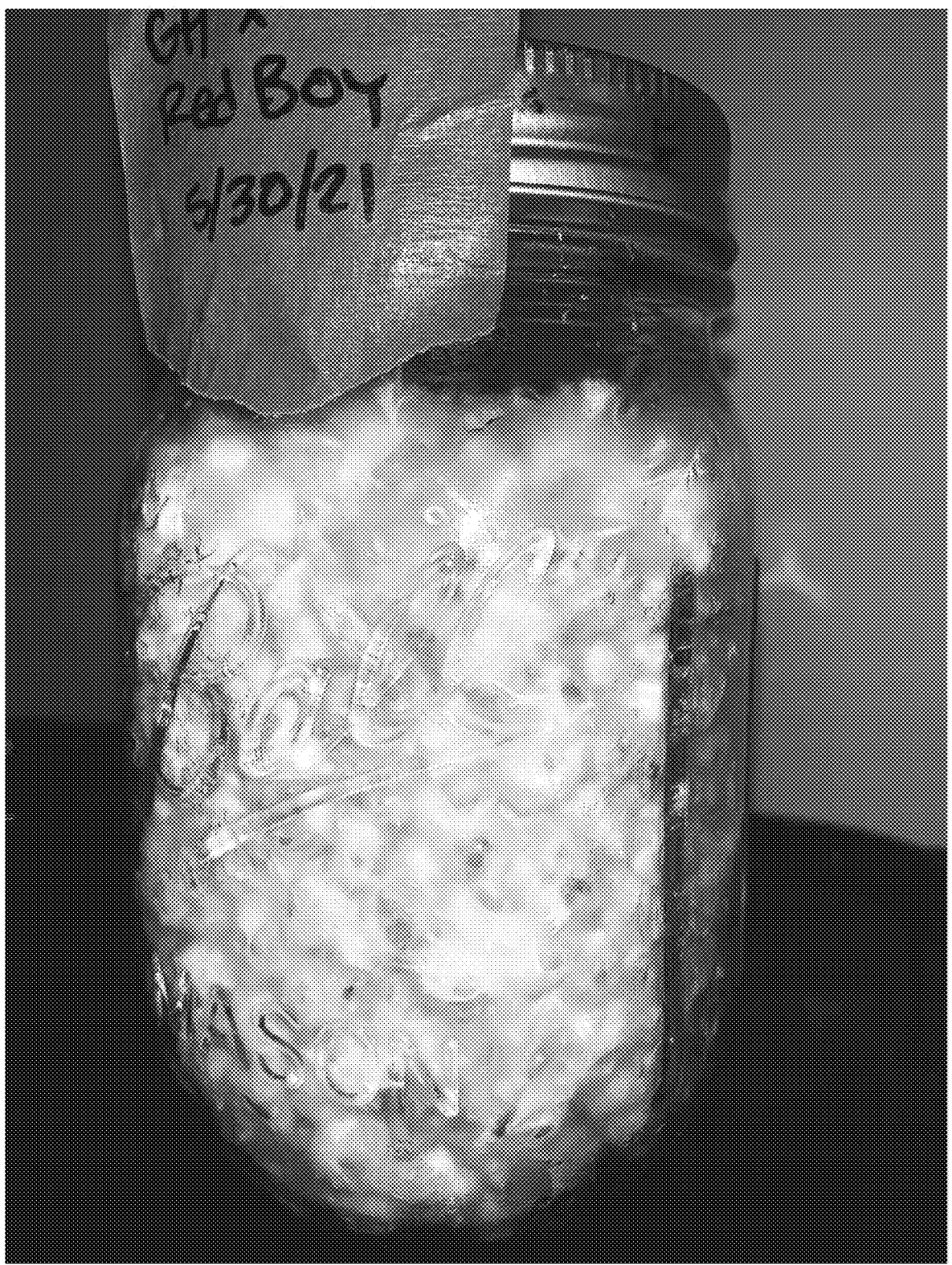
FIG. 8 is a photograph of the crossbred fungus organism shown in FIG. 6 replicating and forming third colonies on a nutrient food source.
Figure 9:
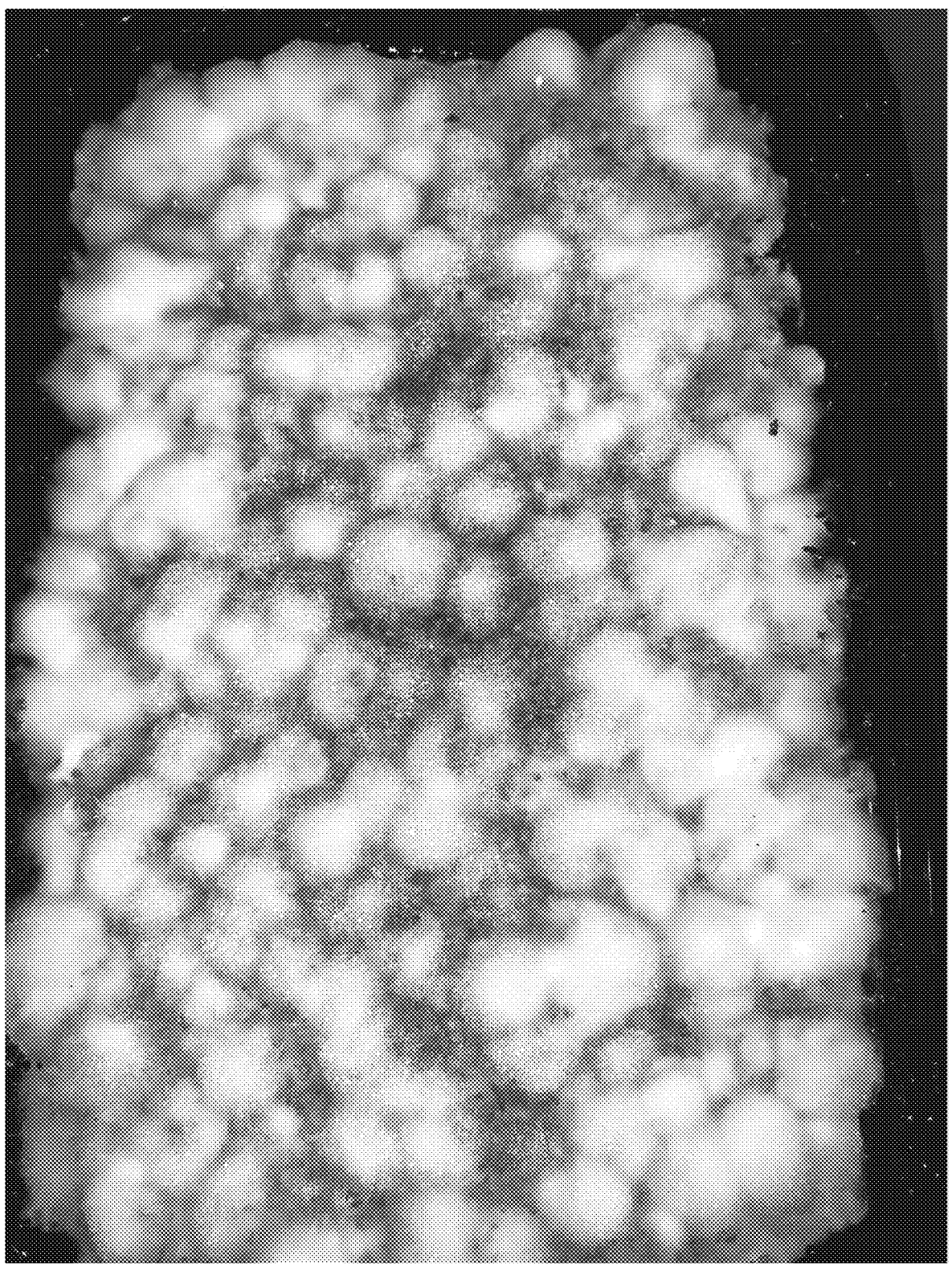
FIG. 9 is a photograph of the crossbred fungus organism shown in FIG. 6 replicating and forming third colonies on a nutrient rich substrate.
Figure 10:
FIG. 10 is a photograph of a fruiting body of a *Psilocybe cubensis* sub-variant known as Golden Halo.
Figure 11:
FIG. 11 is a photograph of a fruiting body of a *Psilocybe cubensis* sub-variant known as Ape.
Figure 12:
FIG. 12 is a photograph of a fruiting body of a novel Golden Oozaru crossbred fungus organism created by the method shown in FIG. 1 starting with a Golden Halo *Psilocybe cubensis* sub-variant and an Ape *Psilocybe cubensis* sub-variant.
Figure 13:
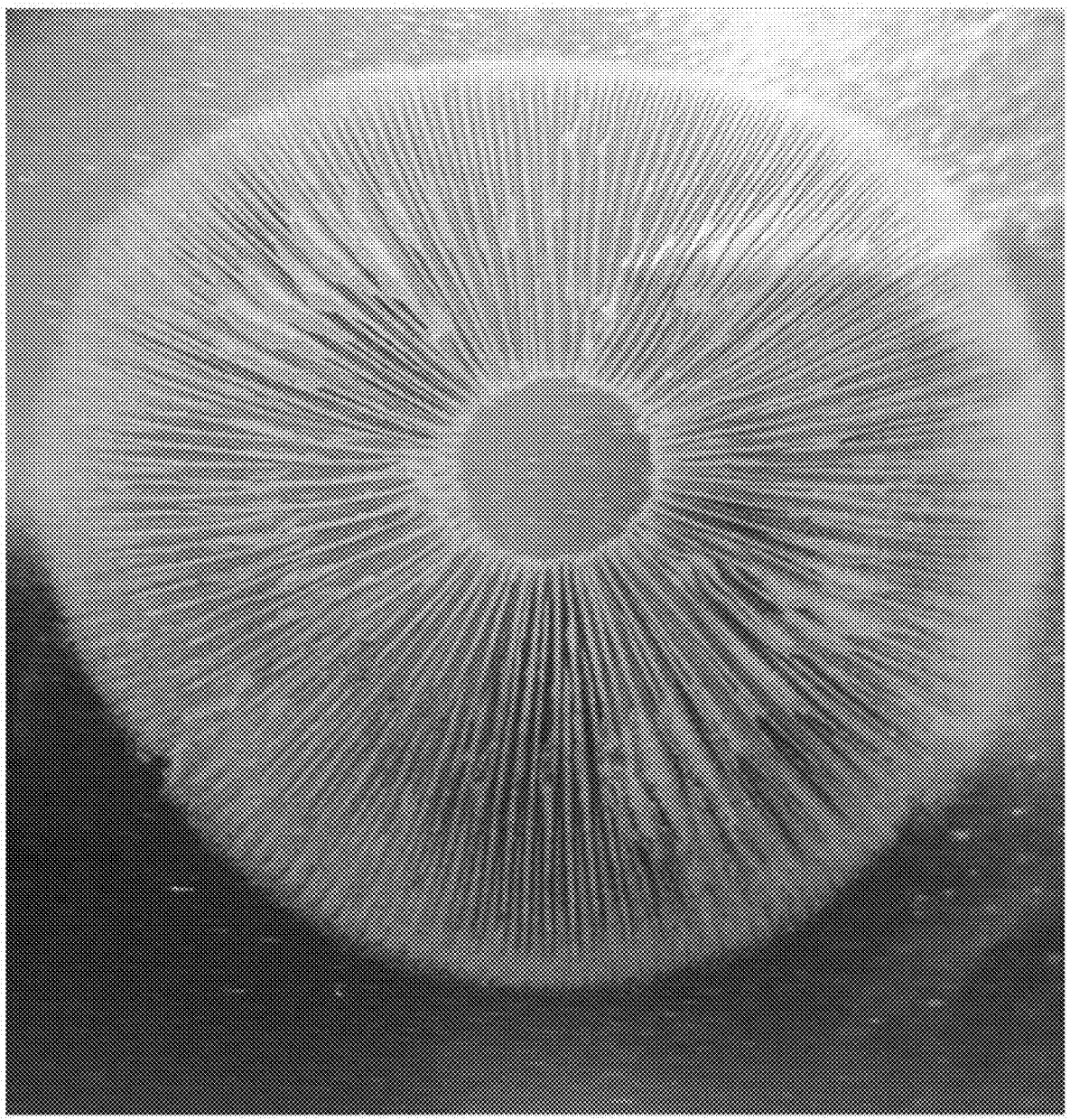
FIG. 13 is a photograph of a golden colored spore from the Golden Halo *Psilocybe cubensis* sub-variant fruiting body shown in FIG. 10.
Figure 14:
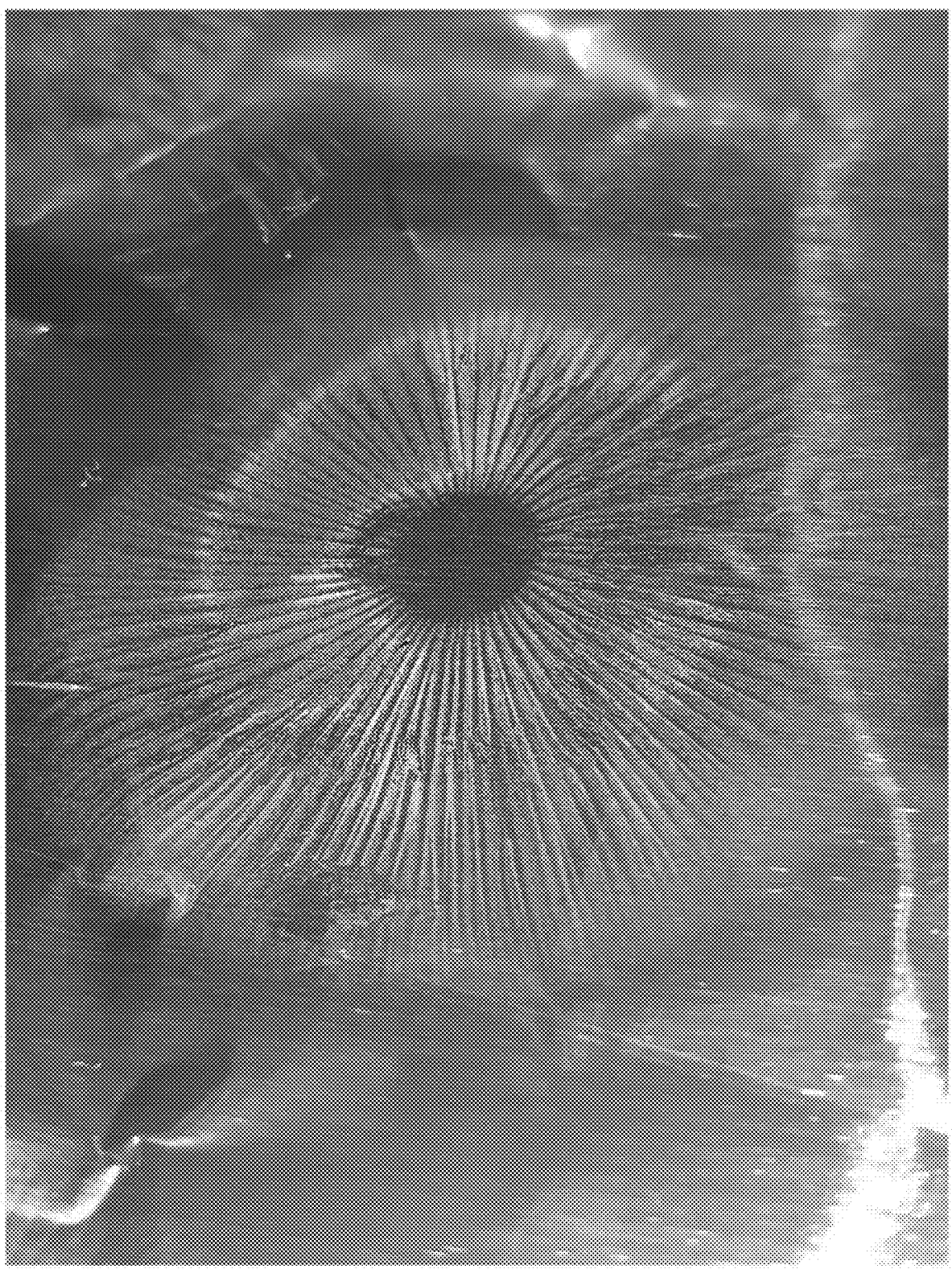
FIG. 14 is a photograph of a pink colored spore from the novel crossbred Golden Oozaru *Psilocybe cubensis* sub-variant fruiting body shown in FIG. 12.
Figure 15:
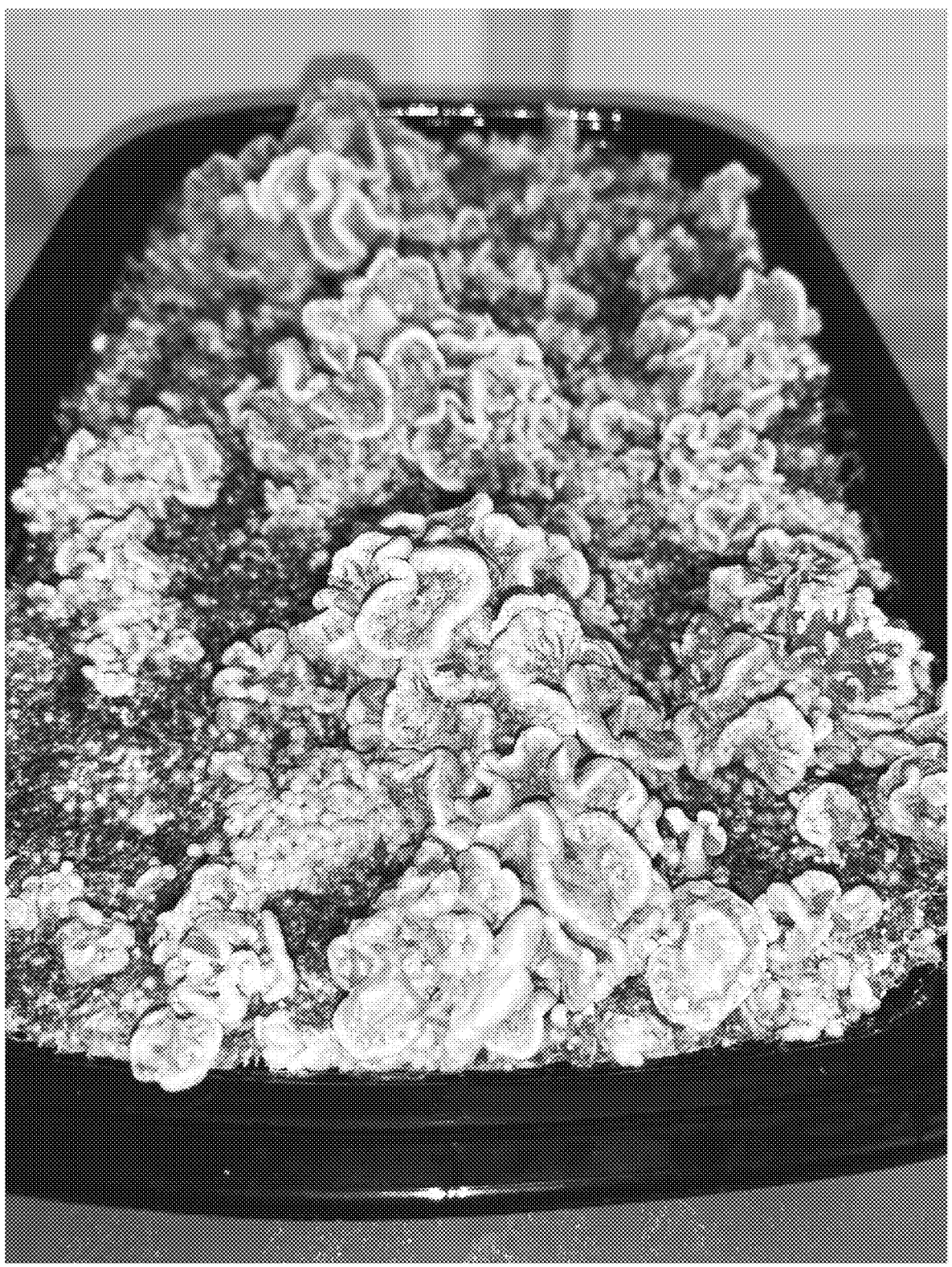
FIG. 15 is a photograph of a fruiting body of a *Psilocybe cubensis* sub-variant known as Enigma.
Figure 16:
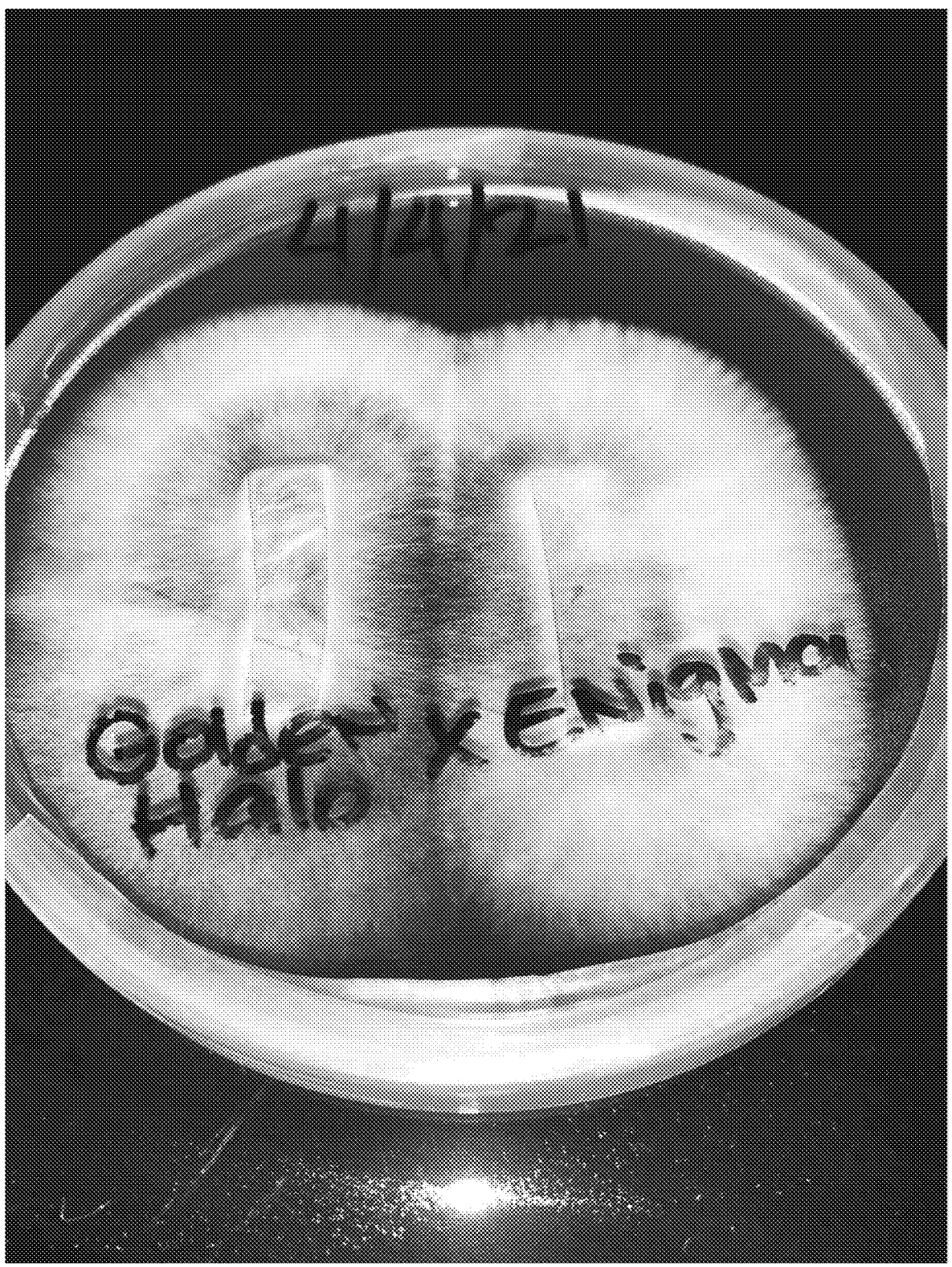
FIG. 16 is a photograph showing the anastomosis fusion of dikaryotic mycelium between the sporeless Enigma *Psilocybe cubensis* sub-variant and a spore producing *Psilocybe cubensis* sub-variant known as Golden Halo.
Figure 17:
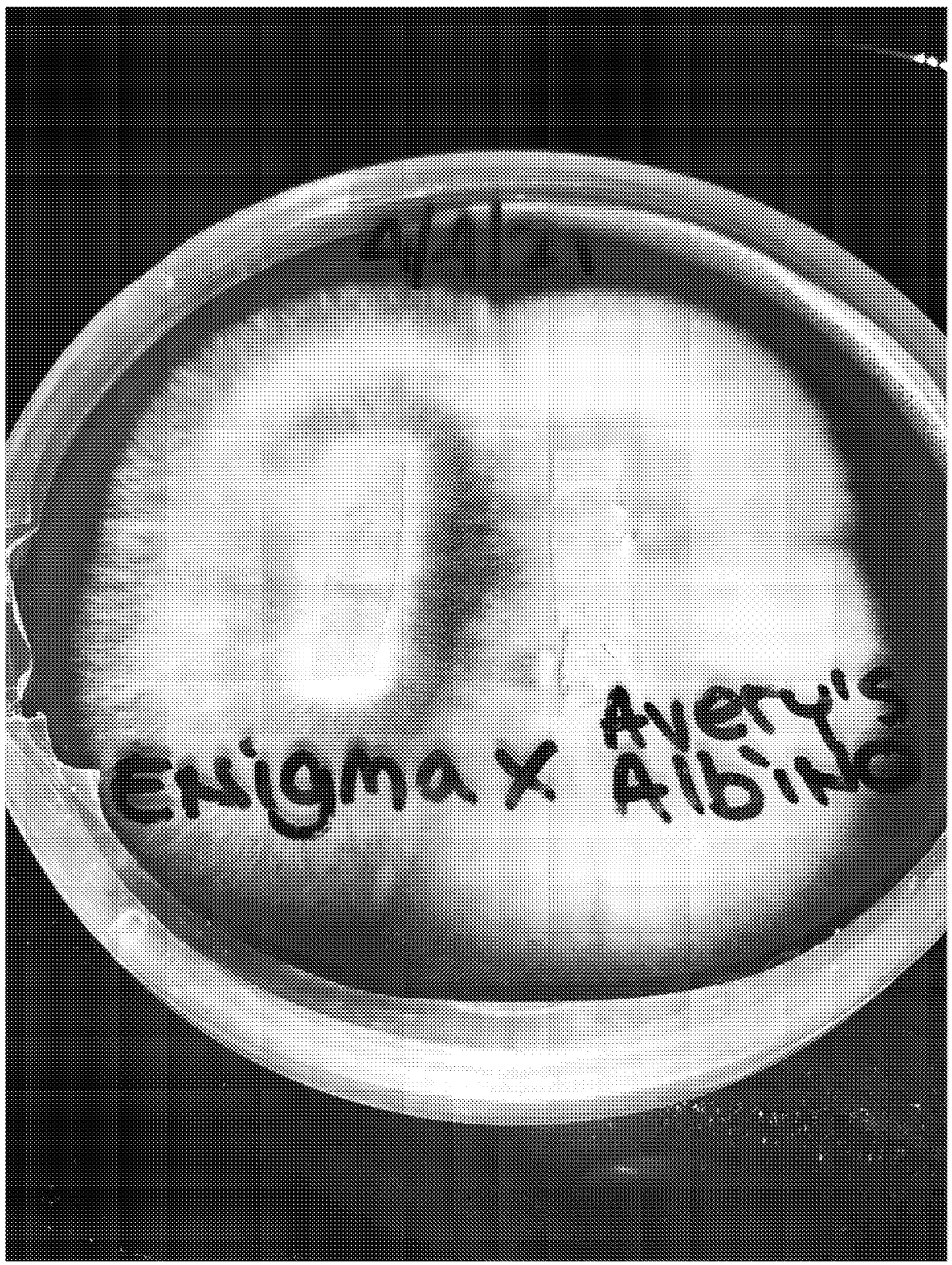
FIG. 17 is a photograph showing the anastomosis fusion of dikaryotic mycelium between the sporeless Enigma *Psilocybe cubensis* sub-variant and a spore producing *Psilocybe cubensis* sub-variant known as Avery's Albino.
Figure 18:
FIG. 18 is a photograph of a fruiting body of a novel crossbred fungus organism, known as Drift Wood, created by the method shown in FIG. 1 starting with a sporeless Enigma *Psilocybe cubensis* sub-variant and a Golden Halo *Psilocybe cubensis* sub-variant depicting an abnormal semi-mutation body and cap type of the novel crossbred fungus organism fruiting body.
Figure 19:
FIG. 19 is a photograph of a fruiting body of a spore producing novel crossbred fungus organism, known as Clear Water, created by the method shown in FIG. 1 starting with a sporeless Enigma *Psilocybe cubensis* sub-variant and an Avery's Albino *Psilocybe cubensis* sub-variant depicting an abnormal semi-mutation body and cap type of the novel crossbred fungus organism fruiting body.
Figure 20:
FIG. 20 is a photograph of a fruiting body of a sporeless and translucent novel crossbred fungus organism, another phenotype of Clear Water, created by the method shown in FIG. 1 starting with a sporeless Enigma *Psilocybe cubensis* sub-variant and a Avery's Albino *Psilocybe cubensis* sub-variant depicting an abnormal semi-mutation body and cap type of the novel crossbred fungus organism fruiting body.
Figure 21:
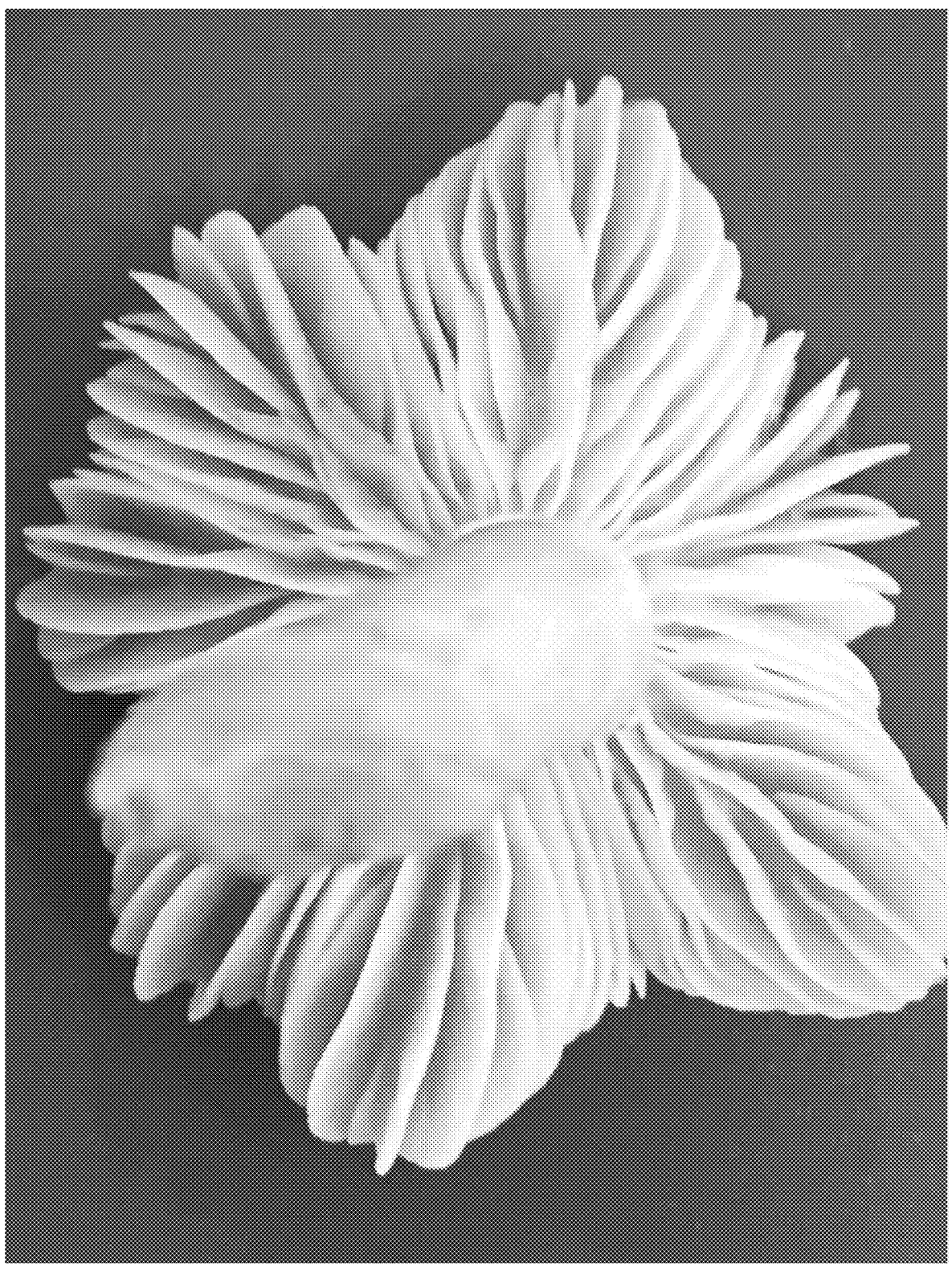
FIG. 21 is a photograph of a fruiting body of a *Psilocybe cubensis* sub-variant known as Louisiana Albino.
Figure 22:
FIG. 22 is a photograph of a fruiting body of a novel Touch of Grey crossbred fungus organism created by the method shown in FIG. 1 starting with an Ape *Psilocybe cubensis* sub-variant and a Louisiana Albino *Psilocybe cubensis* sub-variant.
Figure 23:
FIG. 23 is a photograph of a fruiting body of a novel Angel Wings crossbred fungus organism created by the method shown in FIG. 1 starting with a Golden Halo *Psilocybe cubensis* sub-variant and an Avery's Albino *Psilocybe cubensis* sub-variant.
Figure 24:
FIG. 24 is a photograph showing the anastomosis fusion of dikaryotic mycelium between the Golden Halo *Psilocybe cubensis* sub-variant and a *Psilocybe azurescens* sub-variant.
Figure 25:
FIG. 25 is a photograph showing the anastomosis fusion of dikaryotic mycelium between the Golden Halo *Psilocybe cubensis* sub-variant and a *Psilocybe stuntzii* sub-variant.

The disclosed methods of crossbreeding fungi organisms will become better understood through review of the following detailed description in conjunction with the figures. The detailed description and figures provide merely examples of the various inventions described herein. Those skilled in the art will understand that the disclosed examples may be varied, modified, and altered without departing from the scope of the inventions described herein. Many variations are contemplated for different applications and design considerations; however, for the sake of brevity, each and every contemplated variation is not individually described in the following detailed description.

Throughout the following detailed description, examples of various fungi crossbreeding methods are provided. Related features in the examples may be identical, similar, or dissimilar in different examples. For the sake of brevity, related features will not be redundantly explained in each example. Instead, the use of related feature names will cue the reader that the feature with a related feature name may be similar to the related feature in an example explained previously. Features specific to a given example will be described in that particular example. The reader should understand that a given feature need not be the same or similar to the specific portrayal of a related feature in any given figure or example.

Definitions

The following definitions apply herein, unless otherwise indicated.

"Substantially" means to be more-or-less conforming to the particular dimension, range, shape, concept, or other aspect modified by the term, such that a feature or component need not conform exactly. For example, a "substantially cylindrical" object means that the object resembles a cylinder, but may have one or more deviations from a true cylinder.

"Comprising," "including," and "having" (and conjugations thereof) are used interchangeably to mean including but not necessarily limited to, and are open-ended terms not intended to exclude additional elements or method steps not expressly recited.

Terms such as "first", "second", and "third" are used to distinguish or identity various members of a group, or the like, and are not intended to denote a serial, chronological, or numerical limitation.

"Coupled" means connected, either permanently or releasably, whether directly or indirectly through intervening components.

"Spore-producing mushrooms" means any normal, spore producing, physical expression type fruit body belonging to the fungi genus *Psilocybe* or *Panaeolus*.

"Sporeless mushrooms" means any normal or abnormal physical expression type fruit body belonging to the fungi genera *Psilocybe* or *Panaeolus* that lacks the ability to produce spores.

"Abnormal mutations" means any fruit body that shows any physical expression not normal to *Psilocybe* or *Panaeolus* fungi. Such mutations may include, for example, blob type mutations, fin type mutations, coral type mutations, or any fungi with mutated caps or bodies.

"Sclerotia" means the underground growing, truffle type fruit bodies that certain *Psilocybe* or *Panaeolus* species are capable of producing.

"Monokaryotic" means hyphae and mycelium that contain nuclei of one same genotype. Monokaryotic is interchangeable with heterokaryotic, homokaryotic, and uninucleate.

"Dikaryotic" means mycelium that contain binucleate cells.

"Binucleate" means cells that contain two nuclei.

"Hyphal anastomosis" means cellular fusion between branches of the same or different hyphae or mycelium.

"Hyphae" means individual cellular threads that form when spores germinate.

"Mycelium" means a collection or grouping of hyphae that have formed ropelike threads creating a web-like network.

"Culture" means a product of the cultivation of a living microorganism on a prepared nutrient medium. Such a microorganism may include, for example, *Psilocybe* or *Panaeolus* mycelium.

"Sub-variant" means a subsidiary variant or subtype of a *Psilocybe* or *Panaeolus* species. Such subtypes, for example, may include a wild *Psilocybe* or *Panaeolus* species collected from a certain location or isolated phenotypes of domesticated or wild *Psilocybe* or *Panaeolus* species.

"Domesticated species" means a *Psilocybe* or *Panaeolus* species that has been stabilized from generational selection and line breeding.

"Wild species" means a *Psilocybe* or *Panaeolus* species that has been collected from its natural growing habitat.

"Line breeding" means a form of inbreeding that involves making selections and collecting and growing spores from those selections. The inbreeding process is repeated through multiple generations so that only one or few phenotypes occur more than once within a *Psilocybe* or *Panaeolus* species sub-variant.

"Vegetatively compatible" means compatible to mate in the vegetative or non-fruiting stage of growth.

Methods of Crossbreeding Fungi Organisms

With reference to FIG. 1, methods of crossbreeding fungi organisms will now be described. The methods discussed herein function to crossbreed two distinct fungi organisms through hyphal anastomosis fusion.

The reader will appreciate from the figure and description below that the presently disclosed methods address many of the shortcomings of conventional fungi crossbreeding methods. For example, the novel methods described herein enable crossbreeding two different species of *Psilocybe* or *Panaeolus* fungi whether the fruit bodies produce spores or not. Further, the novel methods described herein enable crossbreeding two different species of *Psilocybe* or *Panaeolus* fungi with far greater success rates than existing methods.

Relevant to therapeutic applications, the novel methods discussed in this application consistently produce above average concentrations of the psychoactive compounds psilocybin, psilocin, and baeocystin. As a result, the fungus organisms created from the novel methods discussed below have far greater potential in a therapeutic context than normal *Psilocybe* or *Panaeolus* fungi. The novel methods discussed herein enable increasing the levels of all three psychoactive compounds, psilocybin, psilocin, and baeocystin, in *Psilocybe* and *Panaeolus* species that are already being widely cultivated, such as, *Psilocybe cubensis* or *Panaeolus cyanescen*, making those species even more desirable to cultivate.

The novel methods discussed in this document further enable adding hybrid vigor to *Psilocybe* and *Panaeolus* species that are already being widely cultivated. The enhanced hybrid vigor makes the *Psilocybe* and *Panaeolus* species easier to cultivate.

With a wide range of potential applications, the novel methods disclosed herein enable creating and defining new novel species of the *Psilocybe* or *Panaeolus* genus. For example, the presently disclosed methods allow for creating novel sub-variants of a *Psilocybe* or *Panaeolus* species with traits desirable to a *Psilocybe* or *Panaeolus* cultivator or to a collector of *Psilocybe* or *Panaeolus* spores. Novel sub-variants created with the novel methods discussed herein may include notable traits like unique spore color, abnormalities in fruit body growth, or a variety of other abnormalities.

Method Embodiment One

With reference to FIG. 1, a first example of a method of crossbreeding fungi organisms, method 100, will now be described. Method 100 includes providing a first growth medium at step 102, placing a first fungus organism on a first growth medium at step 104, and placing a second fungus organism on the first growth medium at step 106. Step 108 of method 100 is allowing the first fungus organism to replicate to form a first colony and step 110 is allowing the second fungus organism to replicate to form a second colony.

At step 112, method 100 includes allowing the first colony and the second colony to expand until they intersect along a clamp line where the first colony and the second colony exchange genetic material between them to yield a crossbred fungus organism. Method 100 continues with harvesting the crossbred fungus organism by removing the clamp line at step 114. At step 116, method 100 includes transferring the clamp line to a second growth medium.

Method 100 further includes allowing the clamp line to replicate and form a third colony at step 118. At step 120, method 100 includes transferring the third colony to a food source. Step 122 of method 100 is allowing the third colony to replicate on the food source.

At step 124, method 100 includes harvesting the third colony after it has replicated. Step 126 of method 100 is transferring the third colony to a substrate. Method 100 further includes allowing the third colony to fruit into a fruiting body at step 128.

An optional step 130 of method 100 may be taken after the first colony and the second colony intersect along a clamp line at step 112. Step 130 is dividing the first growth medium into portions and transferring the portions to separate growth mediums.

In some examples, the methods of cross breeding fungi organisms do not include one or more steps depicted in FIG. 1 for method 100. For example, some method examples do not include steps 114-130 depicted in FIG. 1. Some method examples include a subset of steps 102-130, such as steps 102-112, steps 102-114, or steps 102-116, etc. In one example, the method includes steps 102-112 and step 130. In certain examples, the method includes additional or alternative steps not included in method 100 or depicted in FIG. 1.

Providing a First Growth Medium

Providing a first growth medium at step 102 establishes a shared environment for two distinct fungi organisms to replicate and exchange genetic material through hyphal anastomosis fusion.

The first growth medium may be any currently known or later developed type of growth medium suitable for a given species of fungi. Suitable growth mediums include agar, gellen gum, liquid culture solution, grain, and any other nutrient rich media.

The size and shape of the first growth medium may be selected to suit the needs of a given application. For example, the first growth medium may be supported within a standard petri dish.

Placing Distinct Fungus Organisms on the First Growth Medium

Placing first and second fungus organisms on the first growth medium adjacent to each other at steps 104 and 106 functions to seed the first growth medium with fungi organisms to be crossbred in method 100. In the methods described herein, the first and second fungus organisms are selected from the genus *Psilocybe* or *Panaeolus*. The second fungus organism is selected to be different than the first fungus organism because method 100 functions to crossbreed two distinct fungi organisms.

In some examples, the first fungus organism is selected from the genus *Psilocybe* and the second fungus organism is selected from the genus *Panaeolus*. In other examples, the first fungus organism and the second fungus organism are both selected from the genus *Psilocybe*, but are different *Psilocybe* species or *Psilocybe* species variants. In still other examples, the first fungus organism and the second fungus organism are both selected from the genus *Panaeolus*, but are different *Panaeolus* species or *Panaeolus* species variants. In certain examples, one or more of the first fungus organism and the second fungus organism produces a sporeless fruiting body.

In one particular example, the first fungus organism is *Psilocybe cubensis* and the second fungus organism is *Psilocybe semilanceata*. In another specific example, the first fungus organism is *Psilocybe cubensis* and the second fungus organism is *Psilocybe azurescens*. In a further specific example, the first fungus organism is *Psilocybe mexicana* and the second fungus organism is *Psilocybe galindoi*.

Other fungi organism pairings tested to be suitable for the methods described herein include the Golden Halo variant of *Psilocybe cubensis* and *Psilocybe azurescens*; the Golden Halo variant of *Psilocybe cubensis* and *Psilocybe stuntzii*; and the Enigma variant of *Psilocybe cubensis* and the Roller Coaster variant of *Psilocybe cubensis*. A wide range of fungi organism pairs are contemplated beyond those expressly described. Additional examples of fungi organism pairings are described below in the Specific Examples section below.

Allowing the Fungus Organisms to Replicate

Allowing the first and second fungus organisms to replicate enables first and second colonies of the first and second fungus organisms, respectively, to form at steps 108 and 110. The first and second fungus organisms will draw nutrients from the first growth medium and naturally replicate over time.

The time, temperature, and pressure conditions for steps 108 and 110 may be selected within wide ranges as appropriate for given fungi organisms. In some examples, the fungi organisms on the growth medium are held at room temperature and atmospheric pressure until the first and second colonies have grown large enough to intersect with each other.

Allowing Colonies to Intersect

Allowing the first and second colonies to expand and intersect at step 112 serves to form a clamp line between the colonies. Forming a clamp line enables hyphal anastomosis fusion and exchanges genetic material between the first fungus organism and the second fungus organism. The exchange of genetic material yields a crossbred fungus organism.

The time required for the colonies to expand sufficiently to intersect and form a clamp line at step 112 will depend on a variety of factors. For example, different fungus organisms will have different replication rates and different growth mediums will enable different replication rates for a given fungus organism. The proximity of the two colonies on the first growth medium will also be a factor in the time needed to form a clamp line.

The time, temperature, and pressure conditions for step 112 may be selected within wide ranges as appropriate for given fungi organisms. In some examples, the fungi organisms on the growth medium are held at room temperature and atmospheric pressure until the first and second colonies have grown large enough to intersect with each other.

Dividing and Transferring Portions of the First Growth Medium

Dividing the first growth medium into portions and transferring the portions to separate growth mediums at step 130 after step 112 is an option to accelerate subsequent crossbreeding methods. Utilizing optional step 130 allows subsequent methods to effectively start new methods 100 at step 112. The new growth mediums on which portions of the first growth medium are placed will enable the already established colonies of fungi organisms from the first growth medium to continue replicating and intersecting along clamp lines. Optional step 130 may be described as anastomosis fusion.

Optional step 130 can multiply the crossbred fungus organism formed at step 112 by the divisions made of the first growth medium. For example, dividing the first growth medium into fourths and transferring the divisions to four separate growth mediums to replicate can multiply the crossbred fungus organism by approximately four times. Similarly, dividing the first growth medium into thirds and transferring the divisions to three separate growth mediums to replicate can multiply the crossbred fungus organism by approximately three times.

Harvesting and Transferring a Crossbred Fungus Organism

Harvesting the crossbred fungus organism at step 114 and transferring it to a second growth medium at step 116 serves to lay the foundation for replicating the crossbred fungus organism. Harvesting the crossbred fungus organism at step 114 is accomplished by removing the clamp line formed on the first growth medium (or on a separate growth medium receiving a division of a prior first growth medium if optional step 130 was utilized previously). Removing the clamp line may include cutting out the clamp line from a petri dish.

Transferring the clamp line to a second growth medium at step 116 establishes a new growth environment for the crossbred fungus organism to replicate. The second growth medium may be any currently known or later developed type of growth medium suitable for the crossbred fungus organism. Suitable growth mediums include agar, gellen gum, liquid culture solution, grain, and any other nutrient rich media. In some examples, the second growth medium is the same as the first growth medium.

The size and shape of the second growth medium may be selected to suit the needs of a given application. For example, the second growth medium may be supported within a standard petri dish.

Forming a Third Colony

Allowing the clamp line to replicate and form a third colony on the second growth medium at step 118 increases the quantity of the crossbred fungus organism and prepares it for further replication on a grain food source. The third colony may be allowed to grow until there is a sufficient quantity of the crossbred fungus organism and the third colony is sufficiently viable to be replicated on a grain food source.

The time required to form a sufficiently robust third colony of the crossbred fungus organism at step 118 will depend on a variety of factors. For example, different fungus organisms will have different replication rates and different growth mediums will enable different replication rates for a given fungus organism.

The time, temperature, and pressure conditions for step 118 may be selected within wide ranges as appropriate for given crossbred fungus organisms. In some examples, the crossbred fungus organism on the second growth medium is held at room temperature and atmospheric pressure until the third colony occupies a substantial majority of the second growth medium's top surface area.

Replicating the Third Colony on a Food Source

Transferring the third colony to a food source at step 120 enables the third colony to replicate extensively. The food source may be any currently known or later developed nutrient-rich food suitable for a given crossbred fungus organism. Suitable food sources for step 120 include grains, brans, and mixtures of sawdust and bran.

Allowing the third colony to replicate on the grain food source at step 122 increases the quantity of the crossbred fungus organism and prepares it for fruiting when harvested at step 124 and transferred to a substrate at step 126. The third colony may be allowed to replicate until there is a sufficient quantity of the crossbred fungus organism and the third colony is sufficiently viable to fruit when transferred to a substrate.

The time required to form a sufficiently robust third colony of the crossbred fungus organism on the food source at step 122 will depend on a variety of factors. For example, different fungus organisms will have different replication rates and different food sources will enable different replication rates for a given fungus organism.

The time, temperature, and pressure conditions for step 122 may be selected within wide ranges as appropriate for given crossbred fungus organisms. In some examples, the crossbred fungus organism on the second growth medium is held at room temperature and atmospheric pressure until the third colony occupies a substantial majority of the food source surface area.

Harvesting and Transferring the Replicated Third Colony

Harvesting the crossbred fungus organism at step 124 and transferring it to a substrate at step 126 serves to lay the foundation for fruiting the crossbred fungus organism. Harvesting the crossbred fungus organism from the food source at step 124 is accomplished by separating the food source with the crossbred fungus third colony growing on it from the excess food source that does not have significant amounts of the crossbred fungus third colony growing on it. In some examples, the entire food source is transferred to the substrate at steps 124 and 126.

Transferring the crossbred fungus organism to a substrate at step 126 establishes a fruiting environment for the crossbred fungus organism. The substrate may be any currently known or later developed type of substrate for the crossbred fungus organism. Suitable substrates include manure, wood, and soil.

The size, shape, and quantity of the substrate may be selected to suit the needs of a given application. For example, the substrate may be laid out in trays or beds.

Fruiting the Third Colony

Allowing the third colony to fruit on the substrate at step 128 creates a fruiting body. The fruiting body may be harvested and used for a variety of applications, including therapeutic research and treatments.

In some examples, the fruiting body formed at step 128 has an elevated concentration of one or more psychoactive compounds. The psychoactive compounds with elevated concentrations may be psilocybin, psilocin, and/or baeocystin.

The form and characteristics of the fruiting body will be based on the fungi organisms crossbred and may be quite varied. In some examples, the fruiting body is a spore-producing mushroom. In other examples, the fruiting body is a sporeless mushroom. In certain examples, the fruiting body is a truffle. A wide variety of additional or alternative fruting body phenotypes and characteristics will result from crossbreeding different fungi organisms.

The time required to fruit the third colony into fruiting bodies on the substrate at step 128 will depend on a variety of factors. For example, different fungus organisms will have different fruiting rates and different substrates will enable different fruiting rates for a given fungus organism.

The time, temperature, and pressure conditions for step 128 may be selected within wide ranges as appropriate for given crossbred fungus organisms. In some examples, the crossbred fungus organism on the substrate is held at room temperature and atmospheric pressure until the fruiting bodies occupy a substantial majority of the substrate surface area.

Specific Examples

The methods described above have been used to create many unique fruting bodies of novel crossbred fungus organisms. A few examples of novel fruiting bodies and crossbred fungus organisms produced from the methods described above are described briefly here.

Golden Oozaru

In one specific example, two sub-variants of *Psilocybe cubensis* that are highly desirable to cultivate were used as the first and second fungi organisms. In this example, the first fungus organism is known as Golden Halo. Golden Halo is a sub-variant of *Psilocybe cubensis* first discovered in Jamaica that produces only gold colored spores.

The second fungus organism in the Golden Oozaru example is known as Ape. Ape is a cross between two other sub-variants, P.E. and PF Albino, hence the name Albino PE or Ape. Ape is desirable because of its unique body and cap style and because of its albino, unpigmented, or "clear" spores. Ape is also desirable because it is among the *Psilocybe cubensis* sub-variants that consistently produce above average concentrations of psilocybin, psilocin, and baeocystin.

Each of these sub-variants were crossed together using the methods described herein to create a new, third, sub-variant of *Psilocybe cubensis*, known as Golden Oozaru. The resulting Golden Oozaru is a desirable new novel *Psilocybe cubensis* sub-variant that grows much faster than normal *Cubensis*, but still retains the above average potency of Ape.

Golden Oozaru also produces pink colored spores, which is a very unique trait that makes the sub-variant even more desirable.

Enigma Variant

In one examples, the methods described herein were used to create an abnormal mutation sub-variant of *Psilocybe cubensis* using a *Psilocybe cubensis* variant known as Enigma as the first fungus organism. Enigma is desirable because it is consistently up to three times stronger than any of the other highly potent *Psilocybe cubensis* sub-variants, such as Ape.

The methods described herein were used to achieve anastomosis fusion of dikaryotic mycelium between the sporeless *Psilocybe cubensis* sub-variant, Enigma, and two other spore producing variants, Golden Halo and Avery's Albino. A clamp line was observed between the fungi organisms where the fusion took place on each agar plate. The fruit bodies of the progeny between the sporeless *Psilocybe cubensis* sub-variant, Enigma and the spore producing sub-variant, Golden Halo, were spore producing. The fruit bodies also had an abnormal, semi-mutation body and cap type.

Other Abnormal Mutations of *Psilocybe cubensis*

The methods above were used to create numerous abnormal mutations of *Psilocybe cubensis*. For example, the methods described herein were used to create novel fruiting bodies of a mutation of the *Psilocybe cubensis* sub-variant known as Drift Wood (Enigma×Golden Halo), a mutation of the *Psilocybe cubensis* sub-variant known as Clear Water (Enigma×Avery's Albino); a mutation of the *Psilocybe cubensis* sub-variant known as Touch of Grey (Apex×Louisiana Albino); and a mutation of the *Psilocybe cubensis* sub-variant known as Angel Wings (Golden Halo×Avery's Albino). Each of these mutations expresses traits that are highly desirable to cultivators. Mutations like these also have much higher concentrations of psychoactive compounds than normal mushrooms belonging to the same species.

The disclosure above encompasses multiple distinct inventions with independent utility. While each of these inventions has been disclosed in a particular form, the specific embodiments disclosed and illustrated above are not to be considered in a limiting sense as numerous variations are possible. The subject matter of the inventions includes all novel and non-obvious combinations and subcombinations of the various elements, features, functions and/or properties disclosed above and inherent to those skilled in the art pertaining to such inventions. Where the disclosure or subsequently filed claims recite "a" element, "a first" element, or any such equivalent term, the disclosure or claims should be understood to incorporate one or more such elements, neither requiring nor excluding two or more such elements.

Applicant(s) reserves the right to submit claims directed to combinations and subcombinations of the disclosed inventions that are believed to be novel and non-obvious. Inventions embodied in other combinations and subcombinations of features, functions, elements and/or properties may be claimed through amendment of those claims or presentation of new claims in the present application or in a related application. Such amended or new claims, whether they are directed to the same invention or a different invention and whether they are different, broader, narrower or equal in scope to the original claims, are to be considered within the subject matter of the inventions described herein.

The invention claimed is:

1. A method of crossbreeding dikaryotic fungi organisms, comprising the steps of:
   providing a first growth medium;
   placing a first dikaryotic fungus organism on the first growth medium, wherein the first dikaryotic fungus organism is *Psilocybe cubensis* or a sub-variant thereof;
   placing a second dikaryotic fungus organism on the first growth medium adjacent to the first dikaryotic fungus organism, wherein the second dikaryotic fungus organism is *Psilocybe cubensis* or a sub-variant thereof or *Psilocybe azurescens* and the second dikaryotic fungus organism is different than the first dikaryotic fungus organism;
   allowing the first dikaryotic fungus organism to replicate and to form a first colony on the first growth medium;
   allowing the second dikaryotic fungus organism to replicate and to form a second colony on the first growth medium; and
   allowing the first colony and the second colony to expand until they intersect along a clamp line where the first colony and the second colony exchange genetic material between them to yield a crossbred fungus organism.

2. The method of claim 1, further comprising harvesting the crossbred fungus organism by removing the clamp line from the first growth medium.

3. The method of claim 2, further comprising transferring the clamp line to a second growth medium.

4. The method of claim 3, further comprising allowing the clamp line to replicate and form a third colony.

5. The method of claim 4, further comprising transferring the third colony to a food source.

6. The method of claim 5, further comprising:
   allowing the third colony to replicate on the food source; and
   harvesting the third colony after it has replicated on the food source.

7. The method of claim 6, further comprising:
   transferring the third colony to a substrate; and
   allowing the third colony to fruit into a fruiting body on the substrate.

8. The method of claim 7, wherein the substrate is manure.

9. The method of claim 7, wherein the substrate is wood.

10. The method of claim 7, wherein the fruiting body is a spore-producing mushroom.

11. The method of claim 7, wherein the fruiting body is a sporeless mushroom.

12. The method of claim 7, wherein the fruiting body is a truffle.

13. The method of claim 7, wherein the fruiting body has an elevated concentration of one or more psychoactive compounds selected from psilocybin, psilocin, and baeocystin.

14. The method of claim 1, wherein:
   the first dikaryotic fungus organism is *Psilocybe cubensis* or a sub-variant thereof; and
   the second dikaryotic fungus organism is *Psilocybe azurescens*.

15. The method of claim 1, wherein:
   the first dikaryotic fungus organism is a sub-variant of *Psilocybe cubensis*; and
   the second dikaryotic fungus organism is a sub-variant of *Psilocybe cubensis*.

16. The method of claim 15, wherein:
   the first dikaryotic fungus organism is a sub-variant of *Psilocybe cubensis* commercially known as Golden Halo; and the second dikaryotic fungus organism is a sub-variant of *Psilocybe cubensis* commercially known as Ape.

17. The method of claim 15, wherein:
the first dikaryotic fungus organism is a sub-variant of *Psilocybe cubensis* commercially known as Enigma; and
the second dikaryotic fungus organism is a sub-variant of *Psilocybe cubensis* commercially known as Golden Halo.

18. The method of claim 15, wherein:
the first dikaryotic fungus organism is a sub-variant of *Psilocybe cubensis* commercially known as Enigma; and
the second dikaryotic fungus organism is a sub-variant of *Psilocybe cubensis* commercially known as Avery's Albino.

19. The method of claim 1, wherein one or more of the first dikaryotic fungus organism and the second dikaryotic fungus organism produces a sporeless fruiting body.

20. The method of claim 1, further comprising dividing the first growth medium into portions and transferring the portions to separate growth mediums for each portion after allowing the first colony and the second colony to expand until they intersect.

* * * * *